(12) United States Patent
Liao et al.

(10) Patent No.: US 9,101,043 B2
(45) Date of Patent: Aug. 4, 2015

(54) MICROPLASMA SOURCE AND STERILIZATION SYSTEM INCLUDING THE SAME

(75) Inventors: Jiunn-Der Liao, Tainan (TW);
Chih-Chiang Weng, Tainan (TW);
Hsin-Hung Chen, Tainan (TW);
Tung-Yi Lin, Tainan (TW)

(73) Assignee: NATIONAL CHENG KUNG UNIVERSITY, Tainan (TW)

( * ) Notice: Subject to any disclaimer, the term of this patent is extended or adjusted under 35 U.S.C. 154(b) by 230 days.

(21) Appl. No.: 13/137,709

(22) Filed: Sep. 7, 2011

(65) Prior Publication Data
US 2012/0063966 A1    Mar. 15, 2012

Related U.S. Application Data

(60) Provisional application No. 61/380,419, filed on Sep. 7, 2010.

(51) Int. Cl.
*H05H 1/48* (2006.01)
*A61L 2/14* (2006.01)

(52) U.S. Cl.
CPC .. *H05H 1/48* (2013.01); *A61L 2/14* (2013.01); *H05H 2245/1225* (2013.01)

(58) Field of Classification Search
CPC ..... H05H 1/48; H05H 2245/1225; A61L 2/14
USPC ...................................................... 422/186.04
See application file for complete search history.

(56) References Cited

U.S. PATENT DOCUMENTS

| 6,943,316 B2 * | 9/2005 | Konavko et al. | 219/121.4 |
| 7,608,839 B2 * | 10/2009 | Coulombe et al. | 250/426 |
| 7,777,151 B2 * | 8/2010 | Kuo | 219/121.47 |

OTHER PUBLICATIONS

V Léveillé and S Coulombe, Design and preliminary characterization of a miniature pulsed RF APGD torch with downstream injection of the source of reactive species,Plasma Sources Science and Technology, 2005, p. 467-476, Institute of Physics Publishing.

* cited by examiner

*Primary Examiner* — Kishor Mayekar
(74) *Attorney, Agent, or Firm* — Bacon & Thomas, PLLC (57) ABSTRACT

A microplasma source and a sterilization system including the same are disclosed. The microplasma source includes: a microplasma-generating unit including: a gas transmission chamber having a first inlet and a first outlet wherein the first inlet is used to import a first gas; a protection and heat dissipation chamber of which a side is connected to the inner wall of the first outlet; a dielectric inner tube having a second inlet and a second outlet and penetrating through the protection and heat dissipation chamber, wherein the second inlet is communicated to the gas transmission chamber; an electrode arranged outside at the second outlet and located in the protection and heat dissipation chamber; and a hollow metal tube disposed in the gas transmission chamber and the dielectric inner tube and having a third inlet and a third outlet, wherein the third inlet is used to import a second gas.

10 Claims, 5 Drawing Sheets

MICROPLASMA SOURCE AND STERILIZATION SYSTEM INCLUDING THE SAME

CROSS REFERENCE TO RELATED APPLICATION

This application claims the benefit of filing date of U.S. Provisional Application Ser. No. 61/380,419, entitled "Capillary tube based oxygen/argon micro-plasma system for the inactivation/sterilization of bacteria suspended in aqueous solution" filed Sep. 7, 2010 under 35 USC §119(e)(1).

BACKGROUND OF THE INVENTION

1. Field of the Invention

The present invention relates to a microplasma source and, more particularly, to a microplasma source and a sterilization system suitable for the sterilization of reusable medical apparatus and furthermore for injured or infected tissues inactivation/sterilization.

2. Description of Related Art

When reusable medical apparatus such as surgical or dental medical devices are sterilized, total elimination of all microorganisms such as bacteria, fungi, or viruses from the apparatus has to be confirmed to prevent any possible infection to a next patient. However, currently known sterilization methods such as dry autoclave process, the treatment of chemical bactericide such as ethylene oxide, and physical irradiation will result in different degrees of degradation or damage to the treated surfaces. Therefore, medical facilities commence to adopt low temperature and pressure plasma sterilization. In this kind of plasma sterilization, the electrical energy stimulates extremely excited gas in vacuum and produce ionized particles, meta-stable species, and free radicals which can interact with bacteria and therefore cause damage to microorganism metabolism below 50° C. This method is harmless to the environment (main byproducts are $CO_2$ and $H_2O$) and thus can be used to treat thermolabile and wet-labile medical apparatus.

In order to avoid potential damage to the sterilized medical devices and reduce the operation cost of the in-vacuum low temperature plasma apparatus, non-thermal and normal pressure dielectric barrier discharge (DBD) plasma is currently developed for sterilization. The DBD plasma is produced between two parallel plate electrodes of which one is covered with a dielectric material to avoid undesirable generation of electric arcs. Unfavorable influences caused by high energy applied to generate plasma can be reduced or avoided in the DBD plasma. Highly reactive species to be used for the sterilization of the medical devices can be afforded in the DBD plasma with low energy consumption. Nevertheless, there are limits in the use of the above mentioned DBD plasma because most medical apparatus have irregular shapes, and it is difficult for the DBD plasma to cover all exposed surfaces of the medical apparatus or to act on the bacteria hidden in some apertures thereof. Hence, the sterilization performance of the DBD plasma is limited by the shapes of the medical devices to be treated. In addition, the residual bacteria which escape sterilization are generally found hiding in a wet condition such as an aqueous solution. Thus, the applied method has to ensure complete sterilization of the medical devices containing the aqueous solution. However, if the DBD plasma is used to sterilize the medical devices containing an aqueous solution, the difficulty of ensuring complete sterilization will increase considerably.

Hence, if a microplasma technique is developed to achieve complete sterilization of the medical devices containing an aqueous solution and the technique can be flexibly applied to various appearances or shapes of different samples, the sterilization time and the cost of purchasing related devices can be dramatically decreased, so as to facilitate the development of related fields using this technique.

SUMMARY OF THE INVENTION

The object of the present invention is to provide a microplasma source, which does not need high power consumption and can be minimized into a pen size. In this microplasma source, a hollow inner electrode is employed and the reactive and plasma maintenance gases are supplied in different pathways. Furthermore, the microplasma generation exhibits advantages such as low power consumption, being operable at room temperature, no production of harmful substances, and thus is able to follow the trend of requiring absolute safety and being environmentally friendly.

To achieve the object mentioned above, the microplasma source of the present invention includes: a first gas storage unit used for storage of a first gas; a second gas storage unit used for storage of a second gas; a microplasma-generating unit including: a gas transmission chamber having a first inlet and a first outlet wherein the first inlet is connected to the first gas storage unit and used to import a first gas, a protection and heat dissipation chamber of which a side is connected to an inner wall of the first outlet of the gas transmission chamber, a dielectric inner tube having a second inlet and a second outlet and penetrating through the protection and heat dissipation chamber wherein the second inlet is communicated to the gas transmission chamber, an electrode arranged outside at the second outlet of the dielectric inner tube and located in the protection and heat dissipation chamber, and a hollow metal tube disposed in the gas transmission chamber and the dielectric inner tube and having a third inlet and a third outlet, wherein the third inlet is used to import a second gas; and a power supply unit coupled to the electrode and the hollow metal tube to generate microplasma therebetween.

In the microplasma source of the present invention depicted above, the protection and heat dissipation chamber can serve to dissipate heat from the inner of the microplasma source and protect the inner electrode. The dielectric inner tube can conduct the first gas in the gas transmission chamber to the second outlet thereof and also separate the hollow metal tube from the electrode.

In one aspect of the microplasma source of the present invention, the power supply unit is not particularly limited and can be, for example, a power supply with high frequency, high voltage, and low electric current. Since the hollow metal tube is employed in the microplasma source of the present invention, the first and second gases do not mix in advance until they both arrive between the electrode and the hollow metal tube. Therefore, even if the power supply unit can only output low power, generation of microplasma is still able to occur.

In another aspect of the microplasma source of the present invention, the arrangement of the hollow metal tube is not particularly limited, but preferably parallel to the dielectric inner tube and disposed in the center thereof. Thus, during microplasma generation, the second gas transmitted in the hollow metal tube does not contact the first gas transmitted in the dielectric inner tube until the second gas arrives at the second outlet of the hollow metal tube, so as to introduce the first and second gases in different pathways. Besides, the distance from the electrode to the hollow metal layer is not particular limited, and can be changed according to the kind and the ratio of the introduced gases, the type of power supply used, and other parameters. For example, the distance can be in a range from 1 μm to 10 mm.

Another object of the present invention is further to provide a microplasma sterilization system. In the system, the mixture ratio of the reactive and excitation gases can be regulated to give rapid and complete sterilization of bacteria such as *Escherichia coli, Staphylococcus aureus* and *Bacillus thermophilus* on dry or wet portions of various surfaces, including surfaces of medical apparatus, human skin and oral mucosa, within a short period of time.

In order to achieve the above mentioned object, the microplasma sterilization system of the present invention is used to sterilize a sample and includes: a first gas storage unit used for storage of a first gas; a second gas storage unit used for storage of a second gas; one or more microplasma-generating units, each including: a gas transmission chamber having a first inlet and a first outlet wherein the first inlet is connected to the first gas storage unit and used to import a first gas, a protection and heat dissipation chamber of which a side is connected to an inner wall of the first outlet of the gas transmission chamber, a dielectric inner tube having a second inlet and a second outlet and penetrating through the protection and heat dissipation chamber wherein the second inlet is communicated to the gas transmission chamber, an electrode arranged outside at the second outlet of the dielectric inner tube and located in the protection and heat dissipation chamber, and a hollow metal tube disposed in the gas transmission chamber and the dielectric inner tube and having a third inlet and a third outlet wherein the third inlet is used to import a second gas; and a power supply unit coupled to the electrode and the hollow metal tube to generate microplasma therebetween.

The microplasma sterilization system of the present invention can further include a sample tank used to hold the sample if necessary. Accordingly, if the sample, for example a liquid sample, has no specific shape, it can be loaded in the sample tank for sterilization by the system.

Additionally, in order to avoid the influence of environmental air or moisture on the performance of the system, a positioning sleeve can be disposed outside at the second outlet and connected to the protection and heat dissipation chamber. Accordingly, the system can be separated from environmental air or moisture and the microplasma thereof is also separated from a solid sample or the sample tank at a predetermined distance.

In one aspect of the microplasma sterilization system, the first gas serves as an excitation gas for maintenance of the microplasma. The second gas is reactive and commonly used as a reactive gas. The kind of the first and second gases is not specifically limited. For example, the first gas can be argon or helium, and the second gas can be oxygen or nitrogen. Preferably, the first and second gases are respectively argon and oxygen. In addition, the amount of oxygen is preferably regulated according to the sample to be sterilized, and commonly in a range from more than 0% to 20% or less based on that of argon.

In another aspect of the microplasma sterilization system, the power supply unit is not particularly limited and can be, for example, a power supply with high frequency, high voltage, and low electric current.

In still another aspect of the microplasma sterilization system, the arrangement of the hollow metal tube is not particularly limited, but preferably parallel to the dielectric inner tube and disposed in the center thereof. Thus, during microplasma generation, the second gas transmitted in the hollow metal tube does not contact the first gas transmitted in the dielectric inner tube until the second gas arrives at the second outlet of the hollow metal tube, so as to introduce the first and second gases in different pathways.

In yet another aspect of the microplasma sterilization system, the distance from the sample to the first outlet of the dielectric inner tube is considered as a working distance, and it can be 0.1-10 mm. The sterilization time of the sample can be determined according to the species of the bacteria to be sterilized and microplasma parameters. Such parameters are exemplified as the kinds and ratios of the gases and the working distance. In an example of the present invention, the time for sterilization, i.e. the working time can be approximately in a range of 30-300 seconds.

Accordingly, bacteria on dry or wet portions of the skin, for example oral mucosa, can be sterilized totally by regulating the related parameters such as the power input, the working distance, the working time, the kind of the reaction gas and the mixture ratio of the gases in the microplasma sterilization system of the present invention.

Other objects, advantages, and novel features of the invention will become more apparent from the following detailed description when taken in conjunction with the accompanying drawings.

DETAILED DESCRIPTION OF THE PREFERRED EMBODIMENT

Because of the specific embodiments illustrating the practice of the present invention, one skilled in the art can easily understand other advantages and efficiency of the present invention through the content disclosed therein. The present invention can also be practiced or applied by other variant embodiments. Many other possible modifications and variations of any detail in the present specification based on different outlooks and applications can be made without departing from the spirit of the invention.

The drawings of the embodiments in the present invention are all simplified charts or views, and only reveal elements relative to the present invention. The elements revealed in the drawings are not necessarily aspects of the practice, and quantity and shape thereof are optionally designed. Further, the design aspect of the elements can be more complex.

Example 1

Figure 1:
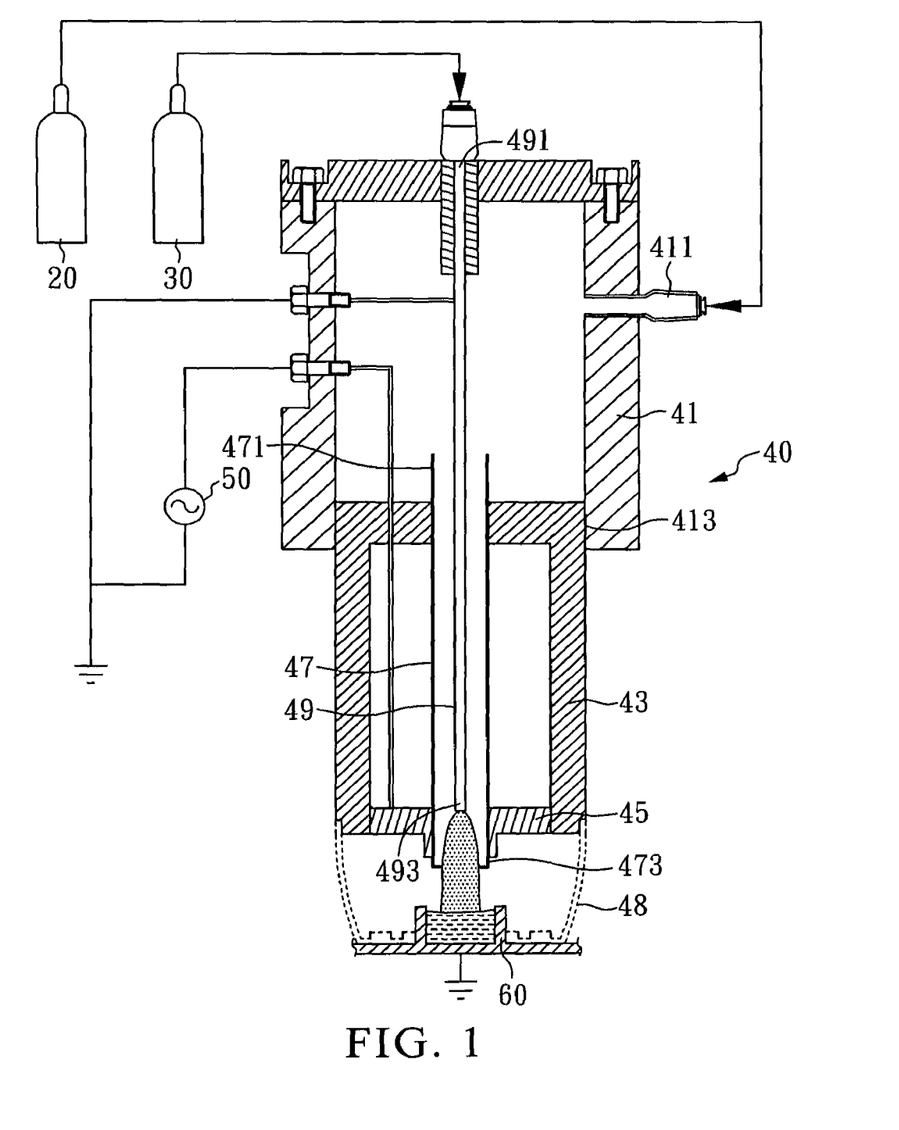
FIG. 1 is a perspective view of the microplasma source in Example 1 of the present invention.

FIG. 1 is a perspective view of the microplasma source in the present example. As shown in FIG. 1, the microplasma source 10 of the present invention mainly includes: a first gas storage unit 20, a second gas storage unit 30, a microplasma-generating unit 40, and a power supply unit 50.

In the present invention, the first gas storage unit 20 is used for storage of a first gas. Likely, the second gas storage unit 30 is used for storage of a second gas. In the present example, the first gas serves as an excitation gas such as argon, and the second gas serves as a reactive gas such as oxygen.

In the microplasma-generating unit 40, a gas transmission chamber 41, a protection and heat dissipation chamber 43, a dielectric inner tube 47, an electrode 45, a hollow metal tube 49, and a positioning sleeve 48 are included. The gas transmission chamber 41 has a first inlet 411 and a first outlet 413. In the gas transmission chamber 41, the first inlet 411 is connected to the first gas storage unit 20 and used to import a first gas. The protection and heat dissipation chamber 43 functions to dissipate heat and protect the inner electrode, and one of its sides is connected to an inner wall of the first outlet 413 of the gas transmission chamber 41. The dielectric inner tube 47 has a second inlet 471 and a second outlet 473, and penetrates through the protection and heat dissipation chamber 43. In the dielectric inner tube 47, the second inlet 471 is communicated to the gas transmission chamber 41 to import the first gas. The electrode 45 is arranged outside at the second outlet 473 of the dielectric inner tube 47 and located in the protection and heat dissipation chamber 43. The hollow metal tube 49 is disposed in the gas transmission chamber 41 and the dielectric inner tube 47 and thus separated from the electrode 45 by the dielectric inner tube 47. The hollow metal tube 49 has a third inlet 491 and a third outlet 493. In the hollow metal tube 49, the third inlet 491 is connected to the second gas storage unit 30 to import a second gas. The positioning sleeve 48 is replaceable and disposed outside at the second outlet 473. The positioning sleeve 48 is connected to the protection and heat dissipation chamber 43 to separate environmental air and moisture from the microplasma and prevent undesired influence on the performance of the microplasma sterilization system. The positioning sleeve 48 is also able to limit the distance between the generated microplasma and a solid sample or the sample tank.

In the present example, a quartz tube having a gas channel and a dielectric coating is able to serve as the dielectric inner tube 47 and in a controlled diameter, for example 5 mm, according to requirements. Besides, a hollow stainless steel tube can be used as the hollow metal tube 49 and in a diameter ranging from 0.5 to 1 mm, for example 0.8 mm. The hollow metal tube 49 is connected to the ground directly and by the power supply unit 50, and functions as an inner electrode to import the second gas. Furthermore, a circular metal conductor such as copper can be used as the electrode 45. The electrode 45 functions as an outer electrode and is electrically connected to the power supply unit 50.

The power supply unit 50 is coupled to the electrode 45 and the hollow metal tube 49 to energize the microplasma-generating unit 40, and thus the microplasma is generated between the electrode 45 and the hollow metal tube 49 of the microplasma-generating unit 40. In the present invention, a radio-frequency (RF, ~13.56 MHz) generator (ACG-3B, ENI, Rochester, N.Y., USA) with a matching network (MW5DM11, ENI) can be used as the power supply unit 50.

Example 2

The microplasma sterilization system of the present example is shown as FIG. 1 and mainly includes: a microplasma source 10, a first gas storage unit 20, a second gas storage unit 30, a microplasma-generating unit 40, and a power supply unit 50. In the present example, the structure of the microplasma sterilization system is substantially the same to that of Example 1. In addition to components delineated above, a sample tank 60 can be further provided to receive a solid or liquid sample if necessary.

Test Example 1

Optical Diagnosis of Excited Species

In the above mentioned microplasma sterilization system of Example 2, argon is used as the first gas and introduced into the gas transmission chamber 41 in a flow rate of $10^4$ sccm. Oxygen is used as the second gas and imported into the hollow metal tube 49 in a flow rate of 0-20 sccm regulated by a mass flow controller (5850E, Brooks Inc.).

The power supply unit 50 is controlled at feeding power of about 27 W ($V_{r.m.s}$~0.57 kV and $I_{r.m.s}$~47 mA). The feeding power can be confirmed with measurement by an oscilloscope (TDS 3034B, Tektronix Inc., OR, USA) with a high voltage probe (P6015A, Tektronix Inc.) and a current probe (P6021, Tektronix Inc.).

A single monochromator (SpectraPro 2300i, Acton Ltd, MA, USA) equipped with a CCD detector (1340×100 pixels) serves as an optical emission spectrometer (OES), and is set at a location away from the outlet of the dielectric inner tube in a distance of 6 mm (i.e., working distance: 6 mm). The generated plasma is diagnosed in-situ by OES. Three gratins are employed: 330~900 nm (150 g/mm), 200~500 nm (1200 g/mm) and 500~1100 nm (1200 g/mm). The spectral resolution is about 0.1 nm with the 1200 g/mm grating.

Figure 2:
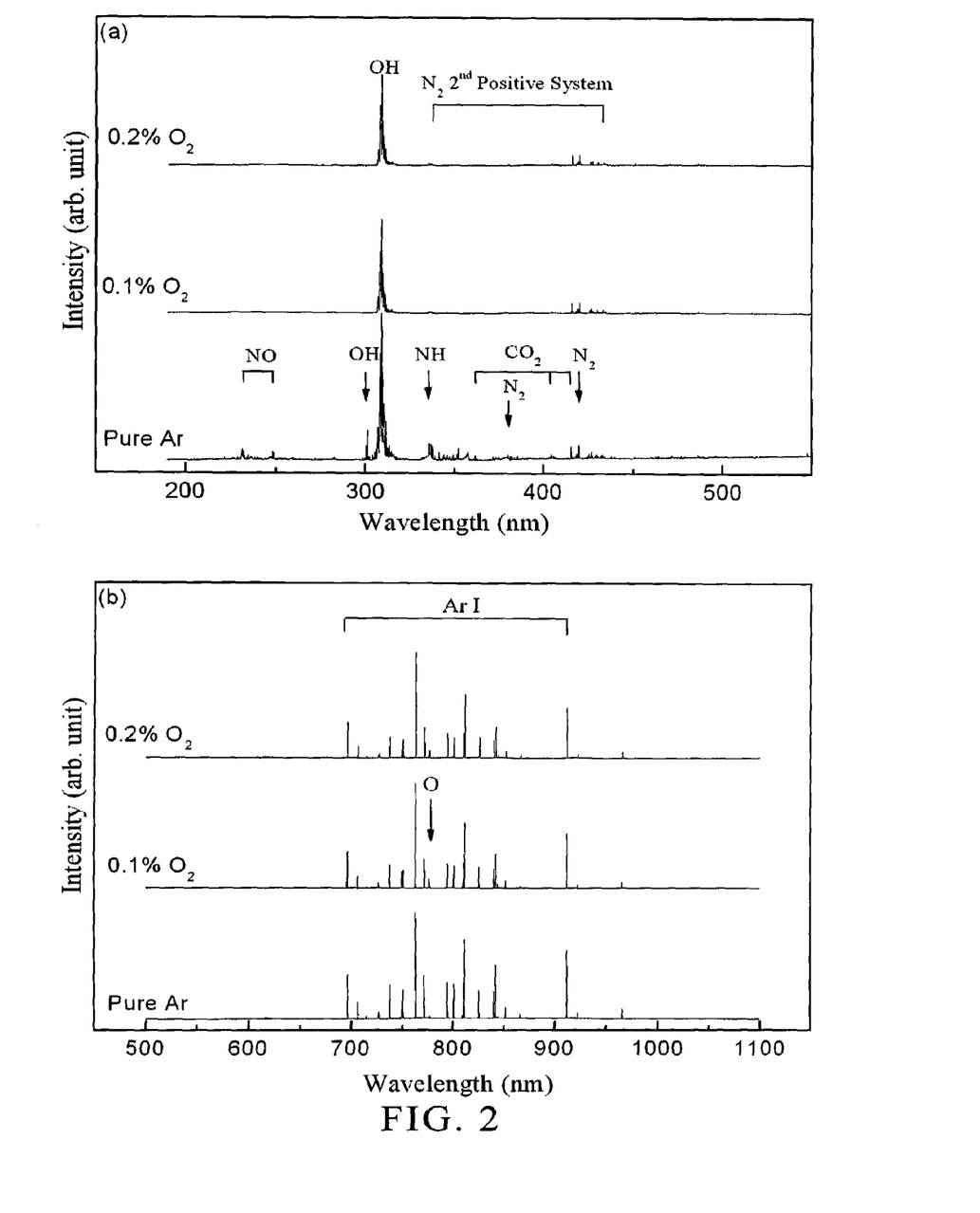
FIG. 2 shows an optical emission spectrometry spectrum in which the working distance of the microplasma is 6 mm in Test Example 1 of the present invention.

The spectral results are shown in FIG. 2. In FIG. 2(a), NO-γ is found at 237 and 248 nm; OH is found at 306 nm; NH is found at 336 nm; $CO_2$ is found at 362, 404, and 416 nm; and $N_2$ ($2^{nd}$ positive system) is found at 331-442 nm. In FIG. 2(b), Ar—I line spectra are found at 696-965 nm and O—I is found at 777 nm.

With reference to FIG. 2, it can be known that chemically reactive N, O-containing species are present in the generated microplasma because ambient air and moisture (e.g., with relative humidity of 65~70%) are participated in the microplasma generation. Furthermore, in FIG. 2(a), compared with the microplasma of pure argon, NO-γ and OH significantly decrease in the microplasma generated from a gas mixture containing 0.1% or 0.2% oxygen in argon. Since the amounts of NO-γ and OH are relative to the intensity of UV emitted from the microplasma, the emission of UV can be reduced efficiently by adding little oxygen into argon during the operation of the system. Moreover, with reference to FIG. 2(b), it can be understood that the O—I species increases with the addition of 0.1% and 0.2% oxygen in argon microplasma. Accordingly, little addition of oxygen is able to change the composition of the microplasma.

Figure 3:
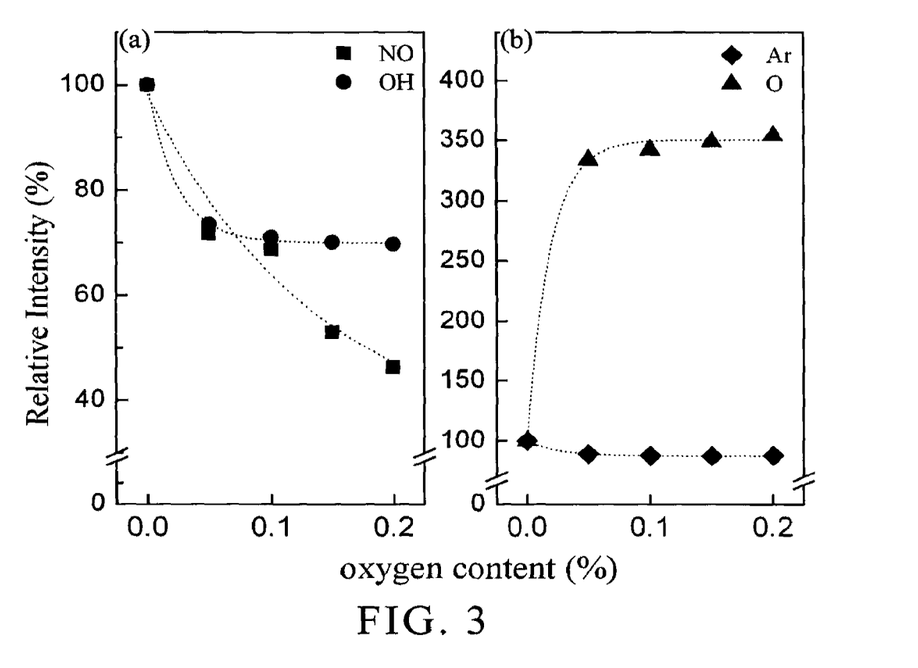
FIG. 3 shows an OES relative intensity diagram of the major species in the microplasma in Test Example 1 of the present invention.

FIG. 3 shows an OES relative intensity diagram of the major species in the generated microplasma. In FIG. 3, (a) represents the amounts of OH and NO; and (b) represents the amounts of O—I and Ar—I. With reference to FIG. 3(a), compared with the microplasma of pure argon, the amount of OH decreases to 75% and 70% and the amount of NO decreases to 70% and 35% with the addition of 0.1% and 0.2% oxygen in argon microplasma. With reference to FIG. 3(b), compared with the microplasma of pure argon, the amount of O—I (777 nm) dramatically increases (about 250%) and the amount of Ar—I (750 nm) slightly decreases (about 10%) with the addition of 0.1% and 0.2% oxygen in argon microplasma. Accordingly, NO and OH generated from the ambient air and moisture decreases owing to little addition of oxygen in argon so that UV emission related to NO and OH is decreased.

Figure 4:
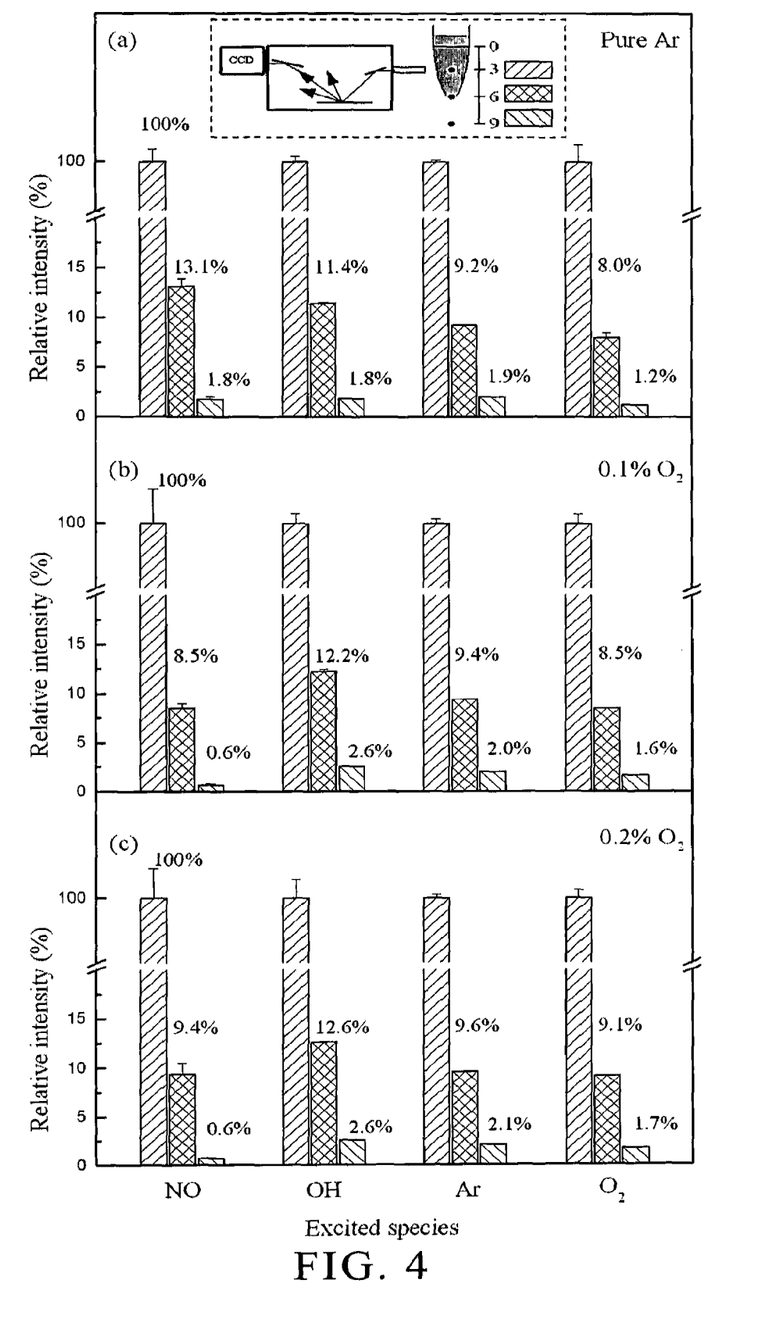
FIG. 4 is a relative intensity-excited species diagram of the microplasma generated in different working distances in Test Example 1 of the present invention.

FIG. 4 is a relative intensity-excited species diagram of the microplasma generated in different working distances. With reference to FIG. 4, as the working distance increases from 3 to 6 mm, only about 10% of the excited species are retained. As the working distance increases to 9 mm, only about 0.6-2.0% of the excited species remains in the microplasma. Therefore, the major species of the microplasma considerably decrease as the working distance increases. If the active species have to be kept in a sufficient amount during action of the microplasma, the working distance is a significant factor.

Test Example 2

Influence of the Sterilization Time

Gram-negative *E. coli* (ATCC 11775) purchased from Culture and Collection Research Center (Shinchu, Taiwan) is cultured on nutrient agar I (Difco 0001, Merck, Darmstadt, Germany) at 37° C. for 24 hr. The bacterium is picked up with a platinum loop and diluted in 10 ml sterilized water. The bacterial suspension is controlled in a concentration of $5 \times 10^6$ CFU/ml.

The bacterial suspension (~200 μl) is placed in the sample tank 60. A conductive metal plate such as an alluminum plate arranged on the bottom of the sample tank and a hollow column made of polydimethyl siloxane (PDMS) arranged on the metal plate form the body of the tank. The related parameters of sterilization are based on those of Test Example 1 except the working distance of 6 mm, the addition of 0-0.2% oxygen in argon, and the sterilization time of 0-180 seconds in the present example. The bacterial suspension posterior to exposure of the microplasma is applied on the nutrient agar plates at 37° C. for 24 hours. The number of bacterial colonies is counted. Both non-treated and plasma-treated *E. coli* samples are diluted with sterilized water and then applied respectively on a pre-washed slide coated with poly-L-Lysine (P8920, Sigma-Aldrich, USA). After freeze-drying for 24 hr, the samples containing the bacteria are coated with a platinum thin layer and examined by a scanning electron microscope (SEM, EVO50, Carl Zeiss, Inc., North America) with the magnification of 4000×.

Figure 5:
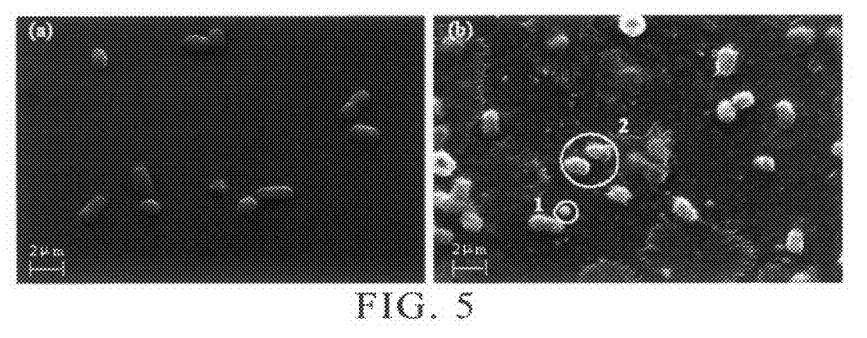
FIG. 5 shows a scanning electron microscopy (SEM) photograph of *E. coli* in Test Example 2 of the present invention, wherein FIG. 5(*a*) denotes the untreated bacteria, and FIG. 5(*b*) represents the bacteria sterilized by microplasma at 6 mm for 120 seconds.

With reference to the SEM photographs of *E. coli* in FIG. 5, FIG. 5(*a*) shows the untreated bacterial cells and FIG. 5(*b*) shows the bacterial cells treated with the microplasma for 120 seconds in the working distance of 6 mm. As shown in FIG. 5(*a*), the untreated bacterial cells keep well in a rod shape. As shown in FIG. 5(*b*), the plasma-treated bacterial cells are curved, irregular, and even broken into pieces.

In addition, the bacterial suspension and the microplasma sterilization system are spaced with a quartz slide in a thickness of 1 mm. Since UV generated from the microplasma is able to pass through the quartz slide, the influence of the generated UV on the bacterial sample can be investigated.

The number of the colonies on the agar is summarized in Table 1. In Table 1, $N_0$ and N are the numbers of the untreated bacterial cells and those treated with microplasma-induced UV, respectively.

TABLE 1

| Exposure time (sec) under plasma-induced UV | Atmospheric argon microplasma | Argon-0.1% oxygen microplasma | Argon-0.2% oxygen microplasma |
| --- | --- | --- | --- |
| | Log ($N_0$/N) | Log ($N_0$/N) | Log ($N_0$/N) |
| 60 | 0.94 | 0.91 | 0.72 |
| 120 | 2.06 | 1.92 | 1.33 |
| 180 | * | 3.25 | 3.07 |
| 240 | * | 3.37 | 3.55 |
| 300 | * | * | * |

* No propagation of *E. coli* is found.

As shown in Table 1, the intensity of UV generated from the microplasma of pure argon is significantly higher than that of the gas mixture containing 0.1% or 0.2% oxygen in argon. If the microplasma of the gas mixture achieves the sterilization only by UV generated therein, the sterilization requires to be performed for a longer time. However, UV is destructive to proteins and nucleic acids in an organism. If the microplasma is used to sterilize the organism, undesirable UV influences mentioned above need to be minimized. Accordingly, the microplasma of pure argon is not suitable for sterilization of the organism due to its high level UV generation. By contrast, the mixture of gases can efficiently reduce the intensity of UV in the generated microplasma.

Besides, other tests to investigate the environmental changes possibly caused by the microplasma sterilization system of Example 2 are also performed. In the results, no sterilization occurs after the bacterial sample is treated with argon airflow at 40° C. for 180 seconds if the power supply unit is turned off. This result indicates that the airflow is not a main cause of sterilization. Moreover, about 70% of the water of the bacterial suspension still remains after plasma-treatment, and the number of the colonies cultured from the plasma-treated bacterial suspension is not significantly reduced. This results means the water loss is not a major cause of sterilization.

In addition, after the bacterial suspension is treated with the microplasma sterilization system for 180 seconds, the liquid temperature is not obviously changed and increased from room temperature, i.e. from 27° C. to 33° C. in the working distance of 6 mm; and from 27° C. to 35° C. and 30° C. in the working distance of 3 and 9 mm, respectively. Compared with a working temperature of about 120° C. in a common autoclave, these temperature changes are not significant to sterilization. This result evidences the source and system of the present invention can also be used on temperature sensitive materials and organisms, for example, such as skin and stomatological application.

The change of the bacterial suspension by the microplasma is reduced from pH 6.5 to 5.2. However, the sterilization is not achieved by the change of the pH value because *E. coli* treated in an acidic solution at pH 3.5 for 10 minutes is able to survive after it is cultured for 24 hours.

Test Example 3

Influences of Working Distance and Sterilization Time

The present test example is performed according to the manners of Test Example 2 described above except the quartz slide between the sample and the microplasma is removed. The related parameters of sterilization are based on those of Test Example 2, but in the present test example, the working distances are 3, 6, and 9 mm; 0%, 0.1%, and 0.2% oxygen is added in argon; and the samples are treated by the microplasma for 0-180 seconds.

The efficiency of the sterilization to E. coli is listed in Table 2. In Table 2, the values are calculated according to the manner of Table 1.

TABLE 2

| Ex- | Oxygen content | | | | | | | | |
|---|---|---|---|---|---|---|---|---|---|
| posure time | Working distance in 3 mm | | | Working distance in 6 mm | | | Working distance in 9 mm | | |
| (sec) | 0% | 0.1% | 0.2% | 0% | 0.1% | 0.2% | 0% | 0.1% | 0.2% |
| 30 | 1.77 | 1.30 | 1.38 | 0.75 | 0.79 | 0.68 | 0.58 | 0.39 | 0.35 |
| 60 | 2.89 | 2.99 | 2.85 | 1.26 | 1.34 | 1.13 | 1.02 | 0.86 | 0.80 |
| 90 | * | * | * | 2.59 | 2.61 | 1.91 | 1.96 | 1.60 | 1.46 |
| 120 | * | * | * | * | * | * | 3.12 | 2.64 | 1.85 |
| 180 | * | * | * | * | * | * | * | * | * |

* No propagation of E. coli is found.

As listed in Table 2, complete sterilization can be achieved within 90 seconds in the working distance of 3 mm, within 120 seconds in the working distance of 6 mm, and within 180 seconds in the working distance of 9 mm.

In conclusion, the microplasma source of the present invention employs a hollow inner electrode and the reactive gas such oxygen is supplied via the inner electrode so that the composition of the microplasma is changed. Thus, the diversity of excited species containing oxygen is raised in the microplasma, but the relative intensity of UV or the production of NO-γ and OH is reduced. The microplasma sterilization to various bacterial species such as E. coli, S. aureus, and B. thermophilus can be optimized in the parameters by suitable regulation of the concentration of the reactive gas, the working distance, and the sterilization time. Even if these bacteria are hidden in a liquid condition, the microplasma source of the present invention is still able to achieve sterilization.

Although the present invention has been explained in relation to its preferred embodiment, it is to be understood that many other possible modifications and variations can be made without departing from the spirit and scope of the invention as hereinafter claimed.

What is claimed is:

1. A microplasma source, comprising:
a first gas storage unit used for storage of a first gas;
a second gas storage unit used for storage of a second gas;
a microplasma-generating unit, comprising:
a gas transmission chamber having a first inlet and a first outlet, wherein the first inlet is connected to the first gas storage unit and used to import a first gas;
a protection and heat dissipation chamber of which a side is connected to an inner wall of the first outlet of the gas transmission chamber;
a dielectric inner tube having a second inlet and a second outlet and penetrating through the protection and heat dissipation chamber, wherein the second inlet is communicated to the gas transmission chamber;
an electrode arranged outside at the second outlet of the dielectric inner tube, disposed between the second outlet of the dielectric inner tube and a third outlet of a hollow metal tube disposed in the gas transmission chamber and the dielectric inner tube, and located in the protection and heat dissipation chamber; and
the hollow metal tube disposed in the gas transmission chamber and the dielectric inner tube, and having a third inlet and said third outlet, wherein the third inlet is used to import a second gas and the third outlet is disposed within the second outlet to form a gas mixing zone; and
a power supply unit coupled to the electrode and the hollow metal tube to generate microplasma therebetween,
wherein the first gas and the second gas mix in the gas mixing zone between the electrode and the hollow metal tube.

2. The microplasma source as claimed in claim 1, wherein the power supply unit is a power supply with high frequency, high voltage, and low electric current.

3. The microplasma source as claimed in claim 1, wherein the hollow metal tube is parallel to the dielectric inner tube and disposed in the center thereof.

4. A microplasma sterilization system used to sterilize a sample, comprising:
a first gas storage unit used for storage of a first gas;
a second gas storage unit used for storage of a second gas;
one or more microplasma-generating units, each comprising;
a gas transmission chamber having a first inlet and a first outlet, wherein the first inlet is connected to the first gas storage unit and used to import a first gas;
a protection and heat dissipation chamber of which a side is connected to an inner wall of the first outlet of the gas transmission chamber;
a dielectric inner tube having a second inlet and a second outlet and penetrating through the protection and heat dissipation chamber, wherein the second inlet is communicated to the gas transmission chamber;
an electrode arranged outside at the second outlet of the dielectric inner tube, disposed between the second outlet of the dielectric inner tube and a third outlet of a hollow metal tube disposed in the gas transmission chamber and the dielectric inner tube, and located in the protection and heat dissipation chamber; and
the hollow metal tube disposed in the gas transmission chamber and the dielectric inner tube, and having a third inlet and said third outlet, wherein the third inlet is used to import a second gas and the third outlet is disposed within the second outlet to form a gas mixing zone; and
a power supply unit coupled to the electrode and the hollow metal tube to generate microplasma there between,
wherein the first gas and the second gas mix in the gas mixing zone between the electrode and the hollow metal tube.

5. The microplasma sterilization system as claimed in claim 4, further comprising: a sample tank used to hold the sample.

6. The microplasma sterilization system as claimed in claim 4, wherein the first gas is argon or helium for maintenance of the microplasma, and the second gas is reactive oxygen or nitrogen.

7. The microplasma sterilization system as claimed in claim 6, wherein the oxygen is contained in an amount of 20% or less based on the argon.

8. The microplasma sterilization system as claimed in claim 4, wherein the power supply unit is a power supply with high frequency, high voltage, and low electric current.

9. The microplasma sterilization system as claimed in claim 4, wherein the hollow metal tube is parallel to the dielectric inner tube and disposed in the center thereof.

10. The microplasma sterilization system as claimed in claim 4, wherein the sample is separated from the first outlet of the gas transmission chamber at a distance ranging from 0.1 to 10 mm.

* * * * *